US011998707B2

(12) United States Patent
Walsh et al.

(10) Patent No.: US 11,998,707 B2
(45) Date of Patent: Jun. 4, 2024

(54) FLOW CONTROL STENT

(71) Applicant: Boston Scientific Scimed, Inc., Maple Grove, MN (US)

(72) Inventors: Michael Walsh, Galway (IE); Javier Palomar-Moreno, Galway (IE); Martyn G. Folan, Galway (IE); Emma J. Mooney, Galway (IE); Shane Moylan, Galway (IE); Thomas Holly, Galway (IE); David Hegarty, Galway (IE); Darren Curran, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 945 days.

(21) Appl. No.: 16/149,234

(22) Filed: Oct. 2, 2018

(65) Prior Publication Data
US 2019/0099589 A1 Apr. 4, 2019

Related U.S. Application Data

(60) Provisional application No. 62/567,679, filed on Oct. 3, 2017.

(51) Int. Cl.
*A61M 27/00* (2006.01)
*A61B 17/11* (2006.01)
*A61B 17/12* (2006.01)

(52) U.S. Cl.
CPC .......... *A61M 27/002* (2013.01); *A61B 17/11* (2013.01); *A61B 17/1114* (2013.01);
(Continued)

(58) Field of Classification Search
CPC ........ A61M 27/002; A61M 2025/0042; A61M 2210/125; A61M 2206/16;
(Continued)

(56) References Cited

U.S. PATENT DOCUMENTS 5,855,601 A * 1/1999 Bessler ................. A61F 2/2418
623/2.38
9,381,041 B2 7/2016 Brown et al.
(Continued)

FOREIGN PATENT DOCUMENTS

JP 2005503881 A 2/2005
JP 2015039515 A 3/2015
(Continued)

OTHER PUBLICATIONS

Yonemura, Y., et al., "Recent advanced in the treatment of peritoneal dissemination of gastrointestinal cancers by nucleoside antimetabolites", Cancer Science 98(1):11-19 (2007).
(Continued)

*Primary Examiner* — Benjamin J Klein
*Assistant Examiner* — Brandon W. Levy
(74) *Attorney, Agent, or Firm* — Seager, Tufte & Wickhem, LLP

(57) ABSTRACT

The present disclosure relates generally to the field of medical devices and establishing fluid communication between body lumens. In particular, the present disclosure relates to devices and methods for establishing a controlled flow or access passage between body lumens. For example, a device may include an elongate tubular body defining a lumen along a length thereof. The elongate tubular body may have an unexpanded configuration and an expanded configuration. In the expanded configuration, a proximal portion of the elongate tubular body may expand into a proximal retention member and a distal portion of the elongate tubular body may expand into a distal retention member, leaving a cylindrical saddle region extending therebetween. The cylindrical saddle region may include a constricted portion configured to move between a first
(Continued)

diameter configuration and a second diameter configuration larger than the first diameter configuration.

18 Claims, 9 Drawing Sheets

(52) U.S. Cl.
CPC .... *A61B 17/12036* (2013.01); *A61B 17/1204* (2013.01); *A61B 17/12172* (2013.01); *A61B 2017/1139* (2013.01); *A61B 17/12177* (2013.01)

(58) Field of Classification Search
CPC .... A61M 2039/064; A61M 2039/0653; A61M 2039/0646; A61M 2039/0666; A61B 17/1114; A61B 17/1204; A61B 17/12172; A61B 17/12177; A61B 2017/1139; A61B 17/12122; A61B 2017/00243; A61B 17/1214; A61B 17/12145; A61B 2017/00867; A61B 17/11–1146; A61B 17/12036–12045; A61B 17/12118; A61B 17/3468; A61F 2/90; A61F 2230/0078; A61F 2230/0067; A61F 2/2412; A61F 2230/0013; A61F 2230/008; A61F 2/2418; A61F 2/86; A61F 2/848; A61F 2220/0016; A61F 2/07; A61F 2002/0068; A61F 2002/823; A61F 2/2475; A61F 2/2409; A61F 2/2469; A61F 2/2476; A61F 2/04; A61F 2002/068; A61F 2/2487; A61F 2/958; A61F 2/24; A61F 2/2436
See application file for complete search history.

(56) References Cited

U.S. PATENT DOCUMENTS

| | | | |
|---|---|---|---|
| 2002/0107565 A1* | 8/2002 | Greenhalgh | A61F 2/2475 623/1.13 |
| 2003/0069646 A1* | 4/2003 | Stinson | A61F 2/2412 623/1.24 |
| 2006/0111770 A1* | 5/2006 | Pavcnik | A61B 17/12022 623/1.13 |
| 2007/0096048 A1* | 5/2007 | Clerc | A61F 2/2476 251/142 |
| 2009/0281557 A1 | 11/2009 | Sander et al. | |
| 2010/0056978 A1* | 3/2010 | Machan | A61M 1/3655 604/9 |
| 2010/0249910 A1* | 9/2010 | McNamara | A61F 2/06 623/1.26 |
| 2011/0130657 A1* | 6/2011 | Chomas | A61F 2/013 604/246 |
| 2012/0083871 A1* | 4/2012 | Ryan | A61F 2/90 623/1.15 |
| 2014/0031951 A1 | 1/2014 | Costello et al. | |
| 2014/0236064 A1 | 8/2014 | Binmoeller et al. | |
| 2016/0256169 A1 | 9/2016 | Ben-Muvhar et al. | |
| 2017/0072173 A1 | 3/2017 | Van Dam et al. | |
| 2017/0231766 A1 | 8/2017 | Hariton et al. | |
| 2017/0252144 A1 | 9/2017 | Hannon et al. | |

FOREIGN PATENT DOCUMENTS

| JP | 2017170238 A | 9/2017 |
|---|---|---|
| WO | 0015149 A1 | 3/2000 |

OTHER PUBLICATIONS

Author unknown, "Counting Cells for Immunology Using Cellometer™ Auto T4 Cell Counter", Nexcelom Bioscience, [online] date unknown [retrieved on Jul. 10, 2019]. Retrieved from Internet URL: http://www.nexcelom.com/Literature/App%20Note%2006005%20Immunology.pdf, 3 pages.

International Preliminary Report on Patentability, Application No. PCT/US2018/053839, dated Apr. 7, 2020, 8 pages.

International Search Report and Written Opinion for application No. PCT/US2018/053839, fsyrf Jan. 22, 2019, 13 pages.

* cited by examiner

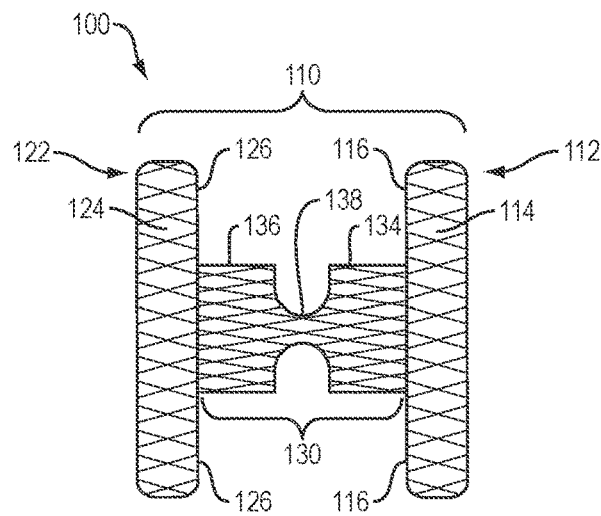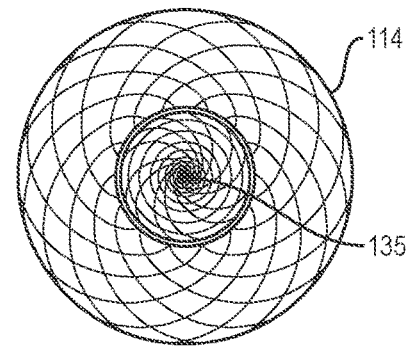
FIG. 1A
FIG. 1B
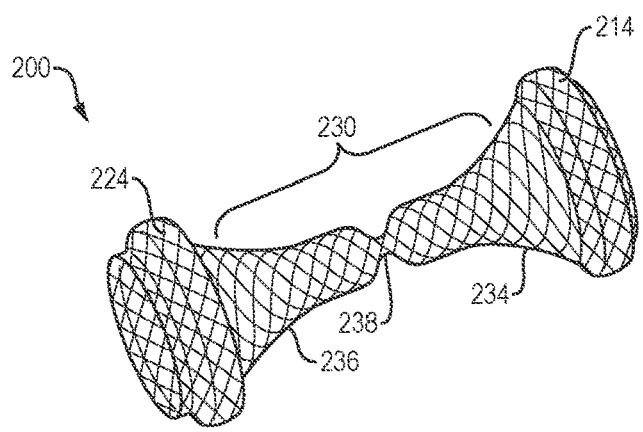
FIG. 2
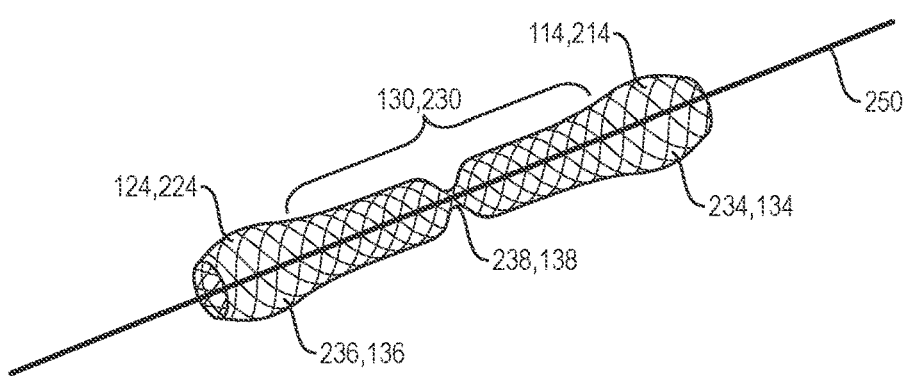
FIG. 3

FLOW CONTROL STENT

CROSS REFERENCE TO RELATED APPLICATIONS

This application claims the benefit of priority under 35 U.S.C. § 119 to U.S. Provisional Patent Application Ser. No. 62/567,679, filed on Oct. 3, 2017, which is incorporated by reference in its entirety for all purposes.

FIELD

The present disclosure relates generally to the field of medical devices and establishing fluid communication between body lumens. In particular, the present disclosure relates to devices and methods for establishing a controlled flow or access passage between body lumens.

BACKGROUND

The desire to establish access between two body lumens to create fluid communication from one to the other is present under various circumstances and conditions. A variety of medical devices (e.g., anastomotic devices, drainage stents, etc.) are able to establish open flow or access passages between body lumens. For example, an anastomotic or drainage device which facilitates transgastric or transduodenal drainage of a symptomatic pancreatic pseudocyst adherent to the gastric or bowel wall may remain implanted for up to 60 days. The open access path provided by the device may allow the continued flow of fluid and/or debris from the pancreatic pseudocyst into the stomach or duodenum. Resolution of the pancreatic pseudocyst may be further enhanced by the flow of acidic stomach fluids into the pseudocyst, which neutralize the alkalinity and increase the viscosity of the fluid and/or debris. While continual unidirectional flow or bi-directional flow through the medical device may be advantageous in certain circumstances, various medical conditions require controlled periodic or intermittent drainage and/or access to a body lumen or organ.

A variety of advantageous medical outcomes may be realized by the devices and/or methods of the present disclosure which allow, for example, infusion and/or drainage of body lumens or organs in a controlled manner for a finite or limited period of time.

SUMMARY

In one aspect, the present disclosure relates to a medical device comprising an elongate tubular body that includes a proximal portion, a distal portion, and a length therebetween, with the elongate tubular body defining a lumen along the length. The elongate tubular body may include an unexpanded configuration, and an expanded configuration wherein the proximal portion expands into a proximal retention member and the distal portion expands into a distal retention member leaving a cylindrical saddle region extending therebetween. The cylindrical saddle region may include a constricted portion configured to move between a first diameter configuration and a second diameter configuration larger than the first diameter configuration. The constricted portion may move from the first diameter configuration to the second diameter configuration in response to a threshold level of force applied to the constricted portion. The constricted portion may be positioned at an approximate midpoint of the cylindrical saddle region. The distal retention member, proximal retention member and/or cylindrical saddle region may include a membrane, covering or coating on an inner and/or outer surface thereof. The elongate tubular body may be formed of one or more braided, woven or knitted filaments. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. Alternatively, a surface of the proximal and distal retention members may be configured to contact an inner surface of an open interior passage of another medical device. The proximal retention member may include a single-walled or double-walled flange structure, and the distal retention member may include a single-walled or double-walled flange structure. The proximal and distal retention members may extend radially from the cylindrical saddle region. A diameter of the proximal and distal retention members may be greater than a diameter of the cylindrical saddle region.

In another aspect, the present disclosure relates to a medical device comprising an elongate tubular body that includes a proximal portion, a distal portion, and a length therebetween, with the elongate tubular body defining a lumen along the length. The elongate tubular body may include an unexpanded configuration, and an expanded configuration wherein the proximal portion expands into a proximal retention member and the distal portion expands into a distal retention member leaving a cylindrical saddle region extending therebetween. A plug may be disposed within the cylindrical saddle region. The plug may be configured to move between a closed configuration and an open configuration. For example, the plug may include at least first and second membranes disposed within a sheath. Each of the first and second membranes may include a least one slit extending through a surface thereof. Each slit may be configured to move from the closed configuration to the open configuration in response to a threshold level force applied to the first and second membranes. An outer diameter of the plug may be equal to or greater than an inner diameter of the cylindrical saddle region. The sheath may include a heat-shrink material. The sheath may include a hydrogel coating configured to swell in an aqueous environment. The distal retention member, proximal retention member and/or cylindrical saddle region may include a membrane, covering or coating on an inner and/or outer surface thereof. The elongate tubular body may be formed of one or more braided filaments. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. A surface of the proximal and distal retention members may be configured to contact an inner surface of an open interior passage of another medical device. The proximal retention member may include a single-walled or double-walled flange structure, and the distal retention member may include a single-walled or double-walled flange structure. The proximal and distal retention members may extend radially from the cylindrical saddle region. A diameter of the proximal and distal retention members may be greater than a diameter of the cylindrical saddle region.

In yet another aspect, the present disclosure relates to a medical device comprising an elongate tubular body that includes a proximal portion, a distal portion, and a length therebetween, with the elongate tubular body defining a lumen along the length. The elongate tubular body may include an unexpanded configuration, and an expanded configuration wherein the proximal portion expands into a proximal retention member and the distal portion expands into a distal retention member leaving a cylindrical saddle region extending therebetween. A cone may be attached to or integrally formed with a portion of the elongate tubular body. The cone may be configured to move between a first diameter configuration and an enlarged second diameter configuration within the cylindrical saddle region in response to a threshold level of force applied to the cone. The proximal retention member, distal retention member, cylindrical saddle region and/or cone may include a membrane, covering or coating on an inner and/or outer surface thereof. The elongate tubular body may be formed of one or more braided filaments. The cone may be integrally formed with, or otherwise attached to, the one or more braided filaments of the elongate tubular body. The cone may include a plurality of overlapping flexible filament loops. The cone may be a nose cone attached to and extending distally beyond the distal retention member. In addition, or alternatively, the cone may be an internal cone disposed within the cylindrical saddle region. The internal cone may be positioned at an approximate midpoint of the cylindrical saddle region. The internal cone may include a portion that tapers in diameter toward the distal retention member. The internal cone may include a portion that tapers in diameter toward the proximal retention member. The elongate tubular body may be formed of one or more braided filaments. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. A surface of the proximal and distal retention members may be configured to contact an inner surface of an open interior passage of another medical device. The proximal retention member may include a single-walled or double-walled flange structure, and the distal retention member includes a single-walled or double-walled flange structure. The proximal and distal retention members may extend radially from the cylindrical saddle region. A diameter of the proximal and distal retention members may be greater than a diameter of the cylindrical saddle region.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A-1B provide side (FIG. 1A) and front (FIG. 1B) perspective views of a medical device, according to one embodiment of the present disclosure.

FIG. 2 provides a perspective view of a medical device, according to one embodiment of the present disclosure.

FIG. 3 provides a perspective view of a medical device, according to one embodiment of the present disclosure.

DETAILED DESCRIPTION

Figure 4A:
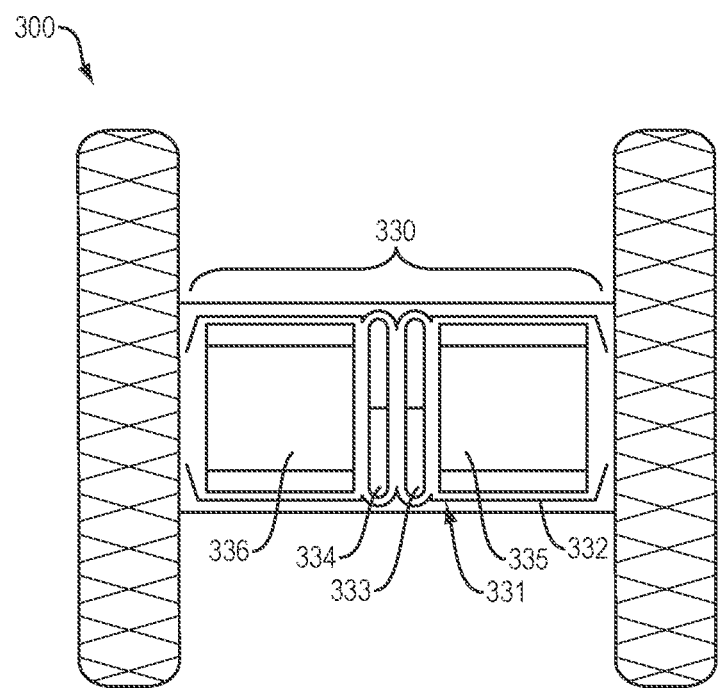
FIGS. 4A-4B provide side (FIG. 4A) and front (FIG. 4B) perspective views of a medical device, according to one embodiment of the present disclosure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices (e.g., anastomotic devices, drainage stents, etc.) and systems to establish and/or maintain a controlled periodic or intermittent flow or access passage from or between the stomach or duodenal wall into the peritoneal cavity, it should be appreciated that such medical devices may be used in a variety of medical procedures, including natural orifice transluminal endoscopic surgery (NOTES) procedures, (e.g., external biliary drain conversion, enteroenterostomy, gastrojejumostomy, gastroduodenostomy and gastroileostomy, transcolonic procedures, transgastric procedures, transtracheal procedures, transvaginal procedures, cholelithiasis procedures, choledocholiathiasis procedures, etc.) to establish and/or maintain a controlled periodic or intermittent flow or access passage from or between a variety of body organs, lumens, ducts, vessels, fistulas, cysts and/or spaces (e.g., the dermis, stomach, duodenum, jejunum, small intestine, gallbladder, kidneys, pancreas, biliary/pancreatic trees, bladder, ureter, abscesses, walled-off pancreatic necrosis (WOPN), bile ducts, etc.). The devices can be inserted via different access points and approaches, e.g., percutaneously, endoscopically, laparoscopically or some combination thereof. The medical devices disclosed herein are self-expanding, but in other embodiments the medical device may be expandable by other means, including, e.g., a balloon catheter. Moreover, such medical devices are not limited to drainage, but may facilitate controlled access to organs, vessels or body lumens for other purposes, such as delivery of therapeutic agents and/or creating a path to divert or bypass fluids or solids from one location to another, removing obstructions and/or non-invasive or minimally invasive manipulation of tissues.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In one embodiment, the present disclosure relates to a medical device (e.g., anastomotic device, drainage stent, etc.) which may allow an efficient mechanism for controlled periodic access to a body lumen or organ to facilitate direct endoscopic delivery of Advanced Therapy Medicinal Products (ATMP's), e.g., immune check-point inhibitors, therapeutic agents, drugs, cellular therapy solutions, etc., for maximal therapeutic effect and minimal patient discomfort. For example, a medical device of the present disclosure may support controlled repeated/intermittent endoscopic delivery of immune boosting therapeutic fluids through the stomach or duodenal wall into a body cavity comprising or adjacent to a diseased organ or tissue.

Referring to FIG. 1A, in one embodiment, a medical device 100 of the present disclosure may include an elongate tubular body 110 forming a lumen and comprising a proximal portion 112, a distal portion 122, a length and a diameter. The elongate tubular body 110 may include an unexpanded configuration (e.g., constrained, undeployed or delivery configuration; not shown), and an expanded configuration (e.g., unconstrained, delivered or deployed configuration) where the proximal portion 112 radially expands into a proximal retention member 114, and the distal portion 122 radially expands into a distal retention member 124, leaving a cylindrical saddle region 130 extending therebetween. A diameter of the cylindrical saddle region 130 may be greater than a diameter of the elongate tubular body 110 in the unexpanded configuration. The proximal and distal retention members 114, 124 may extend radially from (e.g., perpendicular to a circumference of) the elongate tubular body 110 to define respective surfaces 116, 126. The cylindrical saddle region 130 may include a constricted or narrowed portion 138 (e.g., valve) disposed between larger diameter first and second end portions 134, 136. In one embodiment, the constricted portion 138 may be configured to move between a first diameter (e.g., closed) configuration which limits or prevents the flow of fluids and/or debris therethrough, and a second diameter (e.g., open) configuration larger than the first diameter, which provides an open flow or access passage therethrough. For example, as explained in further detail below, the constricted portion 138 may be configured to move from the first diameter configuration to the second diameter configuration in response to a threshold level of force applied to the constricted portion, e.g., as exerted by a medical device advanced through the cylindrical saddle region 130. The medical device 100 may comprise one or more woven, braided and/or knitted filaments, e.g., shape memory materials, which may allow the constricted portion 138 to return to the first diameter configuration upon withdrawal/removal of the medical device from within the cylindrical saddle region 130.

FIG. 1B provides a front perspective view of the medical device 100, with the constricted portion 138 in the first diameter configuration such that substantially no opening or access passage extends through the cylindrical saddle region. In various embodiments, the medical device 100 of the present disclosure is not limited to the configuration depicted in FIG. 1A, but may include a variety of different configurations and/or dimensions. For example, referring to FIG. 2, in one embodiment, a medical device 200 of the present disclosure may include proximal and distal retention members 214, 224 and a cylindrical saddle region 230 with first and second end portions 234, 236 that are tapered in diameter toward the center of the cylindrical saddle region and disposed on either side of the constricted portion 238. FIG. 3 provides a perspective view of the medical device 100, 200 of the present disclosure disposed over a guidewire 250 in a partially deployed configuration. Although the cylindrical saddle region 130, 230 is depicted as a component of medical devices 100, 200 of the present disclosure, in various embodiments, the cylindrical saddle region configuration may be incorporated into any of the medical devices 300, 400, 500, 600 disclosed herein.

Figure 4B:
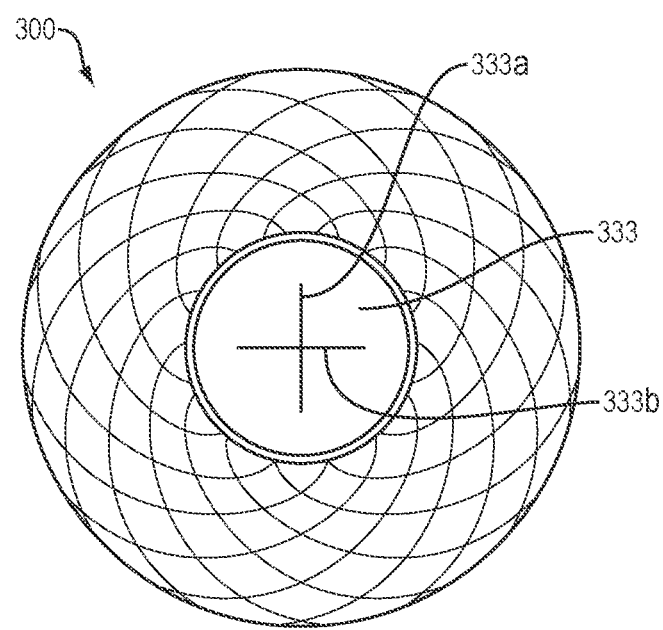
Figure 5A:
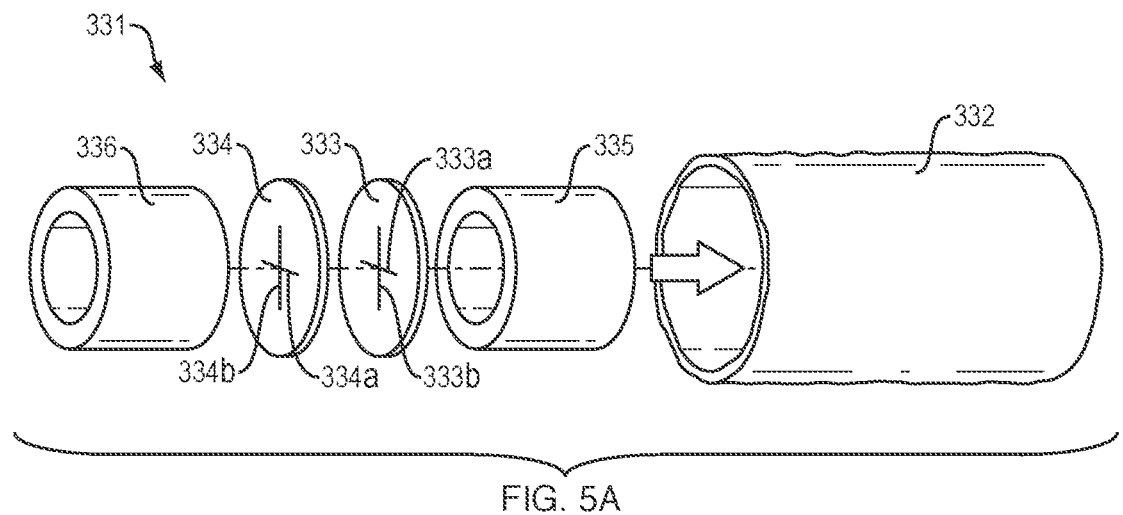
FIGS. 5A-5D provide perspective views of a medical device, according to one embodiment of the present disclosure.

Referring to FIGS. 4A-4B, in one embodiment, a medical device 300 of the present disclosure may include the identical, or similar, configuration and elements as medical devices 100, 200, with the exception that the cylindrical saddle region 330 includes a constant inner and outer diameter. In one embodiment, the medical device 300 may include a plug 331 disposed within the cylindrical saddle region 330. The plug 331 may include first and second membranes 333, 334 disposed within a sheath or housing 332 between first and second washers 335, 336. The first and second membranes 333, 334 may include one or more slits 333a/b, 334a/b (FIG. 5A) configured to move between a first (e.g., closed) configuration which limits or prevents the flow of fluids and/or debris therethrough, and a second (e.g., open) configuration which provides an open flow or access passage therethrough. For example, the slits 333a/b, 334a/b may be configured to move from the first to second configuration in response to a threshold level of force applied to the first and second membranes 333, 334, e.g., as exerted by a medical device advanced through the proximal retention member and into the cylindrical saddle region. In various embodiments, the materials (e.g., foam, rubber, silicone, neoprene, etc.) which comprise the first and second membranes 333, 334 may allow the slits 333a/b, 334a/b to return to the first configuration upon withdrawal/removal of the medical device from within the plug 331.

FIG. 4B provides a front perspective view of the medical device 300, with the slits 333a/b of the first membrane 333 in the first configuration such that substantially no opening or access passage extends through the cylindrical saddle region. Although the membranes 333, 334 of the present disclosure are depicted as substantially circular, in various embodiments, the plug 331 may include any number of membranes (e.g., a single membrane, three or more membranes, etc.) with a variety of sizes, shapes, configurations and/or thicknesses. Similarly, although the slits 333a/b, 334a/b formed within the membranes 333, 334 are depicted as a pair of slits intersecting in an "X" or crosshair configuration, in various embodiments, the number, length, arrangement and/or orientation of the slits may vary.

Figure 5B:
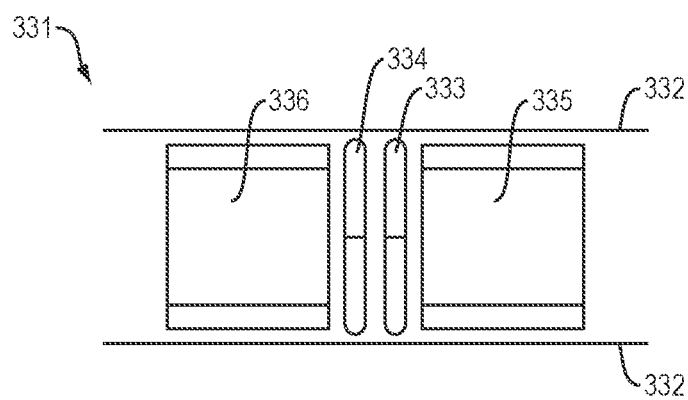
Figure 5C:
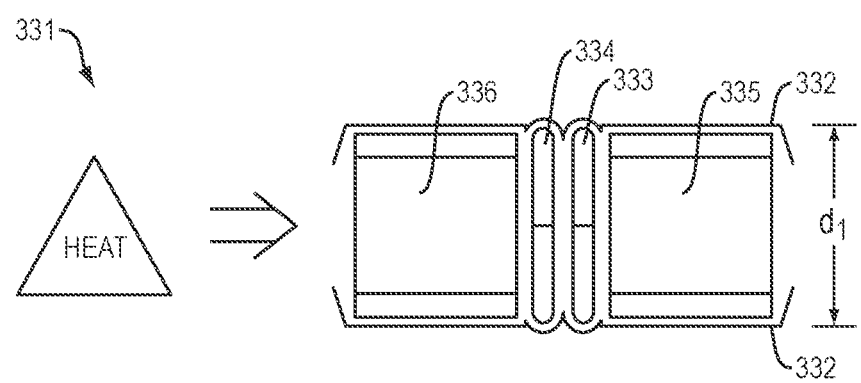
Figure 5D:
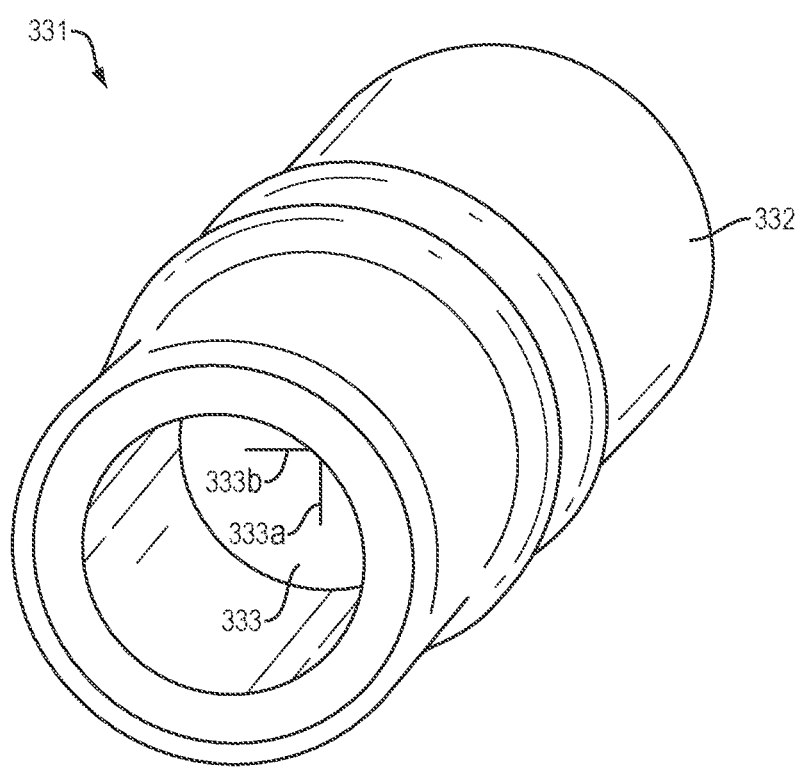

Referring to FIGS. 5A-5D, in one embodiment, the plug 331 may be assembled by positioning the first and second membranes 333, 334 within the sheath 332 between the first and second washers 335, 336. Each of the first and second washers 335, 336 may define an open interior passage to permit flow therethrough. As depicted in FIG. 5B, each of the first and second membranes 333, 334 and first and second washers 335, 336 may be separated by a predetermined distance or space within the sheath 332. Referring to FIG. 5C, in one embodiment, the sheath 332 may include a polymeric or plastic material configured to collapse or shrink (e.g., heat shrink material) upon exposure to an elevated temperature (e.g., 100° C.-150° C.) to lock or secure the position/orientation of the first and second membranes 333, 334 and first and second washers 335, 336 therein. In one embodiment, the assembled and heat-shrunk plug 331 may include an outer diameter $d_1$ (FIG. 5C) which is substantially equal to, or slightly greater than, an inner diameter $d_2$ (FIG. 4A) of the cylindrical saddle region 330, such that the sheath 332 may form a friction, compression or interference fit with a portion of the inner wall of the cylindrical saddle region 330. In addition, or alternatively, the sheath 332 may be coated or impregnated with a hydrogel material which expands or swells upon contact with aqueous fluids (e.g., body fluids) to firmly engage the outer surface of the sheath 332 with the inner wall of the cylindrical saddle region 330.

Although the plug 331 is depicted as a component of medical device 300 of the present disclosure, in various embodiments, the plug may be incorporated into any of the medical devices 100, 200, 400, 500, 600 disclosed herein.

Figure 6A:
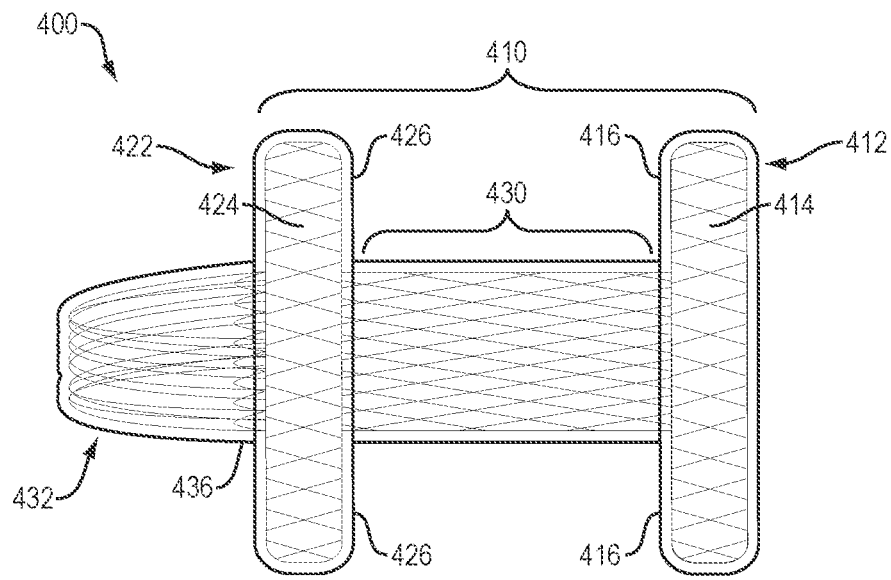
FIGS. 6A-6B provide side (FIG. 6A) and front (FIG. 6B) perspective views of a medical device, according to one embodiment of the present disclosure.
Figure 6B:
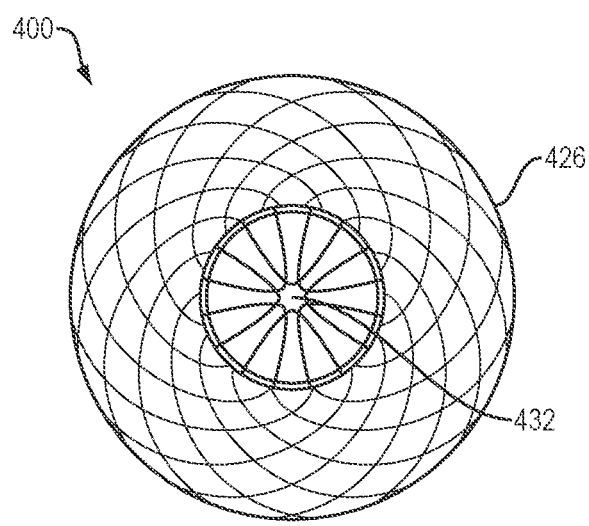

Referring to FIG. 6A, in one embodiment, a medical device 400 of the present disclosure may include an elongate tubular body 410 forming a lumen and comprising a proximal portion 412, a distal portion 422, a length and a diameter. The elongate tubular body 410 may include an unexpanded configuration (e.g., constrained, undeployed or delivery configuration; not shown), and an expanded configuration (e.g., unconstrained, delivered or deployed configuration) where the proximal portion 412 radially expands into a proximal retention member 414, and the distal portion 422 radially expands into a distal retention member 424, leaving a cylindrical saddle region 430 with a constant inner and outer diameter extending therebetween. A diameter of the cylindrical saddle region 430 may be greater than a diameter of the elongate tubular body 410 in the unexpanded configuration. The proximal and distal retention members 414, 424 may extend radially from (e.g., perpendicular to a circumference of) the elongate tubular body 410 to define respective surfaces 416, 426. A nose cone 432 comprising a plurality of flexible overlapping loops may extend distally beyond the distal retention member 424. Each of the loops may include a membrane, covering or coating on an inner and/or outer surface thereof. In one embodiment, the nose cone 432 may be integrally formed with the woven, braided and/or knitted filaments, which comprise the elongate tubular body 410. In addition, or alternatively, a proximal end 436 of the nose cone 432 may be affixed to the distal retention member using a suitable glue, adhesive, resin, solder or other bonding techniques, as are commonly known in the art. In one embodiment, each of the plurality of flexible overlapping loops may include a curled or tapered shape to form a nose cone 432 configured to move between a first diameter (e.g., closed) configuration which limits or prevents the flow of fluids into the cylindrical saddle region, and a second diameter (e.g., open) configuration larger than the first diameter configuration, which provides an open flow or access passage therethrough. For example, the nose cone 432 may be configured to move from the first to second diameter configurations in response to a threshold level of force applied to the nose cone, e.g., as exerted by a medical device advanced through the proximal retention member, cylindrical saddle region and distal retention member. The plurality of loops, e.g., comprised of shape memory fibers or filaments, may allow the nose cone 432 to return to the first diameter configuration upon withdrawal/removal of the medical device from within the cylindrical saddle region. FIG. 6B provides a front perspective view of the medical device 400, with the distal ends of each of the plurality of flexible overlapping loops in the first configuration (e.g., in contact with each other) such that substantially no opening or access passage extends through the nose cone 432 into the cylindrical saddle region.

In various embodiments, the surfaces of the proximal retention members, e.g., of medical devices 100, 200, 300, 400, may atraumatically engage a (e.g., inner) tissue wall of a first body lumen, and the surfaces of the distal retention members may atraumatically engage a (e.g., inner) tissue wall of a second (e.g., adjacent or apposed) body lumen to prevent or limit movement/migration of the deployed medical device within or between the first and second body lumens. Alternatively, in one embodiment, the respective surfaces of the proximal and distal retention members may atraumatically engage opposite sides of a single tissue wall to prevent or limit movement/migration of the deployed medical device.

Figure 7:
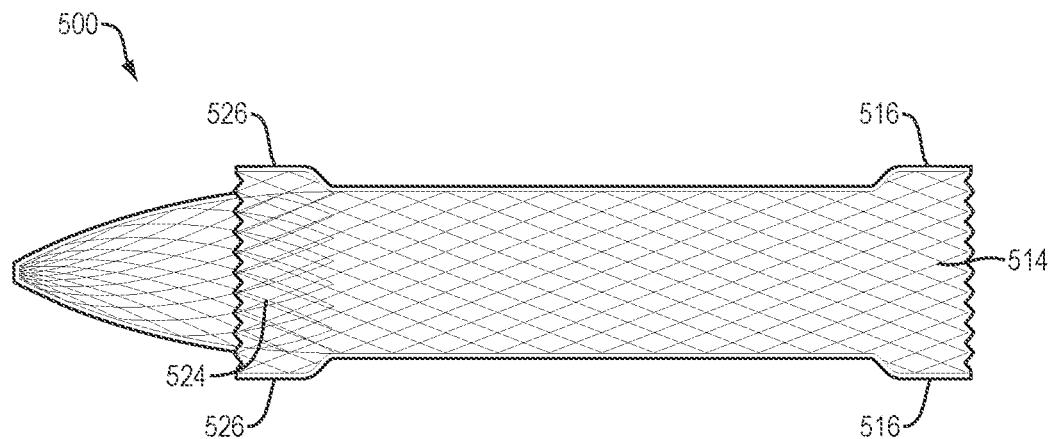
FIG. 7 provides a side perspective view of a medical device, according to one embodiment of the present disclosure.

In one embodiment, a medical device of the present disclosure may be configured to be disposed within an open interior passage of another medical device (e.g., a conventional drainage stent), prior to the other medical device being deployed, or after the other medical device has been deployed, in order to provide periodic flow and/or access therethrough. For example, referring to FIG. 7, in one embodiment, a medical device 500 of the present disclosure may include the identical, or similar, configuration and elements as medical device 400, with the exception that the proximal and distal retention members 514, 524 include an elongate (e.g., "land flare") configuration with respective flat surfaces 516, 526 configured to engage the inner surface of a separate medical device within which the medical device 500 is deployed, as discussed below.

Figure 8A:
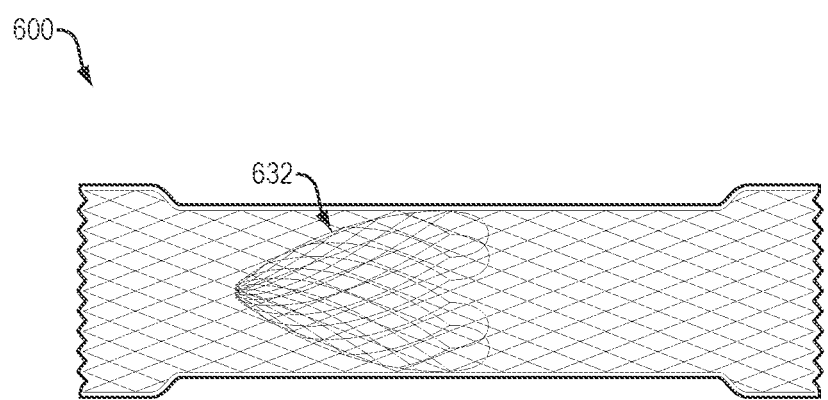
FIGS. 8A-8C provide side perspective views of a medical device, according to one embodiment of the present disclosure.

Referring to FIG. 8A, in one embodiment, a medical device 600 of the present disclosure may include the identical, or similar, configuration and elements as medical device 500, with the exception that the nose cone is replaced with an internal cone 632 disposed within the cylindrical saddle region. The internal cone may include a portion that tapers in diameter toward the distal retention member. In various embodiments, the internal cone 632 may include a plurality of loops, e.g., comprised of shape memory fibers or filaments, integrally formed with the filament braid comprising the cylindrical saddle region. As above, each of the loops may include a membrane, covering or coating on an inner and/or outer surface thereof. In addition, or alternatively, an outer surface of the internal cone 632 may be affixed within the cylindrical saddle region using a suitable glue, adhesive, resin, solder or other bonding techniques, as are commonly known in the art. As above, in one embodiment, each of the plurality of flexible overlapping loops may include a curled or tapered shape to form a distally-facing internal cone 632 configured to move between a first diameter (e.g., closed) configuration which limits or prevents the flow of fluids and/or debris through the cylindrical saddle region, and a second diameter (e.g., open) configuration larger than the first diameter configuration, which provides an open flow or access passage therethrough. For example, the internal cone 632 may be configured to move from the first to second diameter configuration in response to a threshold level of force applied to the internal cone, e.g., as exerted by a medical device advanced through the proximal retention member, cylindrical saddle region and distal retention member. Shape memory fibers or filaments, which may comprise the plurality of flexible loops, allow the internal cone 632 to return to the first diameter configuration upon withdrawal/removal of the medical device from within the cylindrical saddle region. Although depicted in FIG. 8A in a body with a "land flare" configuration, as described above with reference to FIG. 7, an internal cone, integrally formed with or affixed to a body, may be utilized in the body with any of the various flange configurations described herein.

Figure 8B:
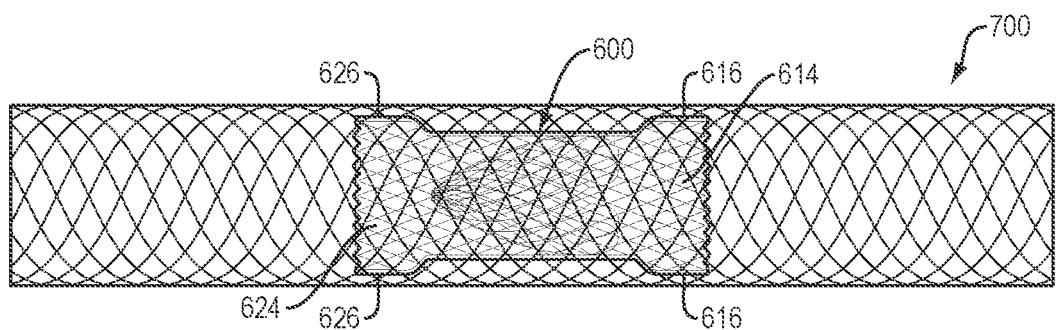
Figure 8C:
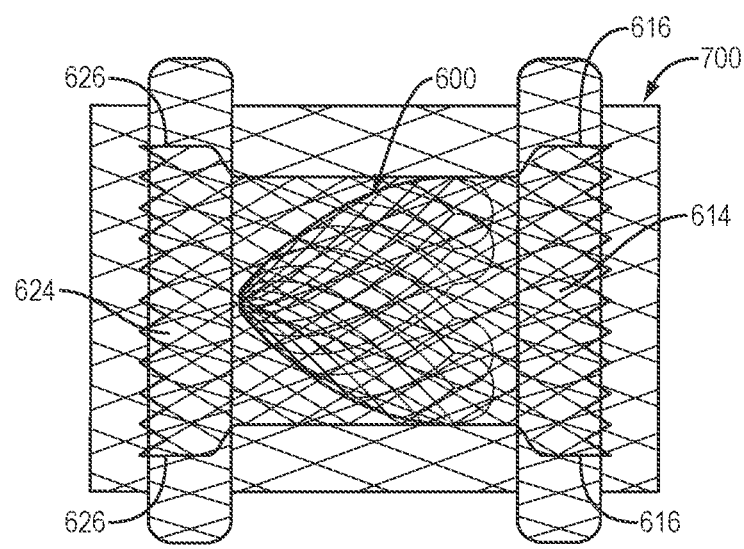

Referring to FIGS. 8B-8C, in various embodiments, the medical device 600 may be disposed within a previously deployed conventional drainage stent 700 to convert the open interior passage into a periodic flow or access passage, as discussed above. The respective surfaces 616, 626 of the proximal and distal retention members 614, 624 may frictionally engage an inner surface of the previously deployed conventional medical device 700 to prevent migration of the medical device 600 therein. Although FIGS. 8B and 8C depict medical device 600 disposed within the lumen (FIG. 8B) or cylindrical saddle region (FIG. 8C) of a conventional self-expanding drainage stent 700, in various embodiments the medical device 500 of FIG. 7 may also be disposed within a previously deployed conventional drainage stent.

Figure 9A:
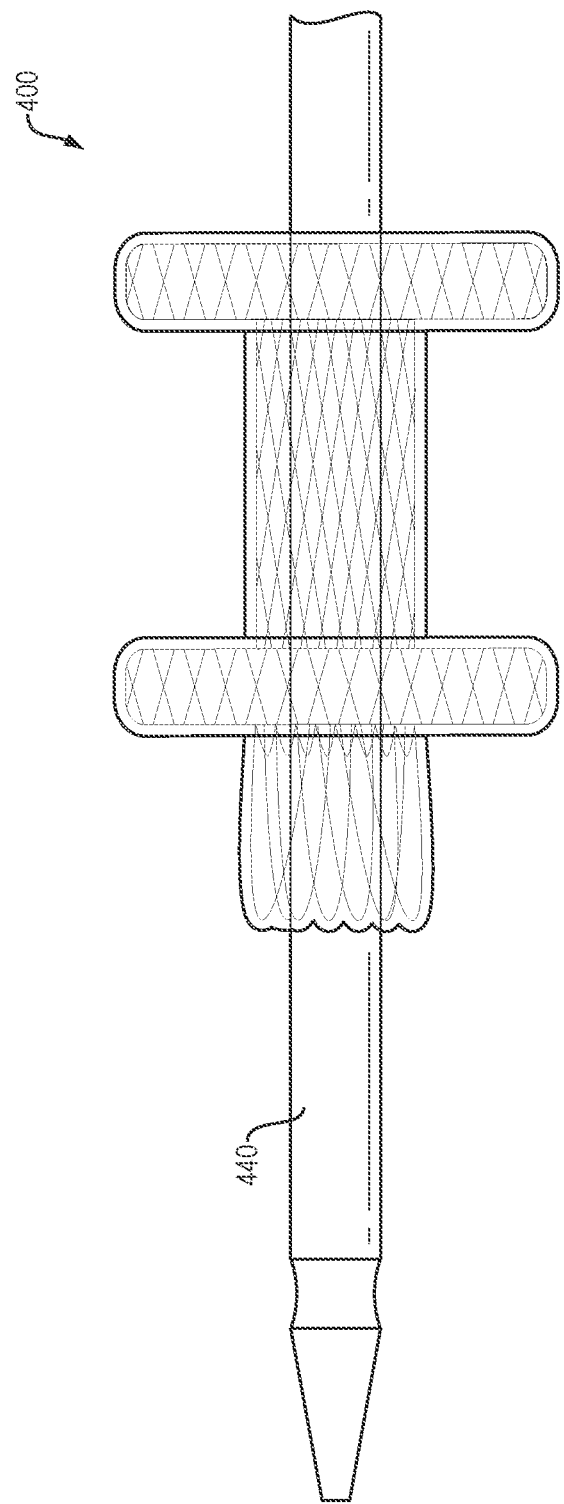
FIGS. 9A-9B provide side perspective views of a medical device, extending through a medical device according to one embodiment of the present disclosure.
Figure 9B:
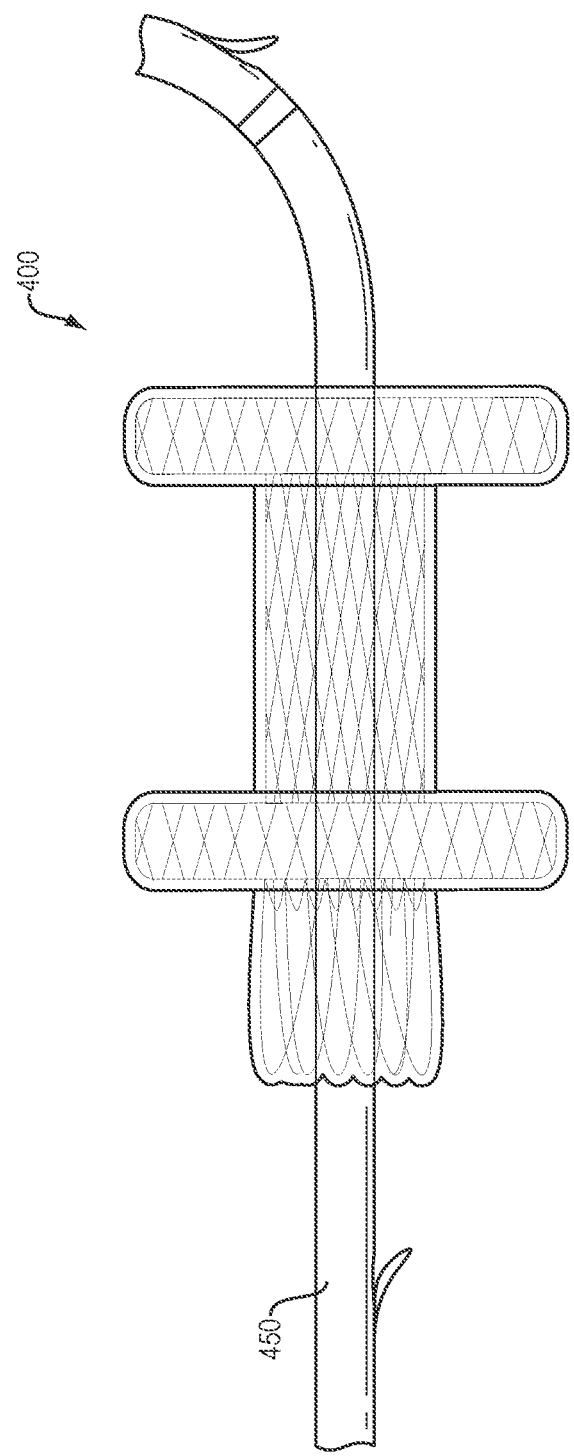

Referring to FIG. 9A, in one embodiment, a user may advance a medical tool 440 (e.g., drainage catheter, infusion catheter, micro-infusion catheter, etc.) through a previously implanted medical device 400, e.g., under endoscopic guidance, and with or without the aid of a previously placed guidewire for the medical tool. In various embodiments, the medical tool 440 may deliver a therapeutic agent into a cavity or space surrounding or adjacent to a diseased tissue or organ. In addition to delivering an effective dose of the therapeutic agent directly within the target body lumen for maximum beneficial effect, the ability of the medical device 400 with, e.g., nose cone, to move between the closed and open configurations, may allow a prolonged regimen (e.g., weeks, months or years) of one or more therapeutic agents to be administered without causing undue discomfort to the patient. In addition, or alternatively, the medical tool 440 may be configured to lavage and/or suction fluid and/or debris from within an abscess or pseudocyst. Referring to FIG. 9B, in another embodiment, a drainage device 450 (e.g., pigtail stent, etc.) may be positioned within a previously implanted medical device 400, e.g., under endoscopic guidance to provide an open flow path therethrough. Once the medical tool (FIG. 9A) or drainage device (FIG. 9B) is proximally withdrawn from within the medical device 400, the nose cone may return to the first (e.g., closed) position to limit and/or prevent flow therethrough. Although FIGS. 9A-9B depict a medical tool 440 or drainage device 450 introduced through a previously implanted medical device 400, in various embodiments these (and other) medical tools and drainage devices may be introduced through any of the medical devices 100, 200, 300, 500, 600 disclosed herein.

In use and by way of example, a medical device 100, 200, 300, 400 of the present disclosure may be disposed in the unexpanded configuration within the lumen of a delivery catheter which may include a tissue-penetrating element. A sharpened distal end of the tissue-penetrating element may be advanced through the tissue wall of a first body lumen (e.g., the stomach or duodenum) and through the tissue wall of a second body lumen (e.g., the peritoneal cavity). Additionally, or alternatively, the tissue penetrating element may comprise a conductive element (e.g., halo wire cone with proximally extending arms) that is configured to receive heat or energy (e.g., RF energy) for the purpose of creating openings.

In various embodiments, the tissue penetrating element may be advanced over a guidewire previously advanced through the first and second body lumens such that a distal end of the guidewire is disposed within the second body lumen. Alternatively, in the method above, a separate instrument with a sharpened distal tip may be advanced along the path above and into the second body lumen to create a path. A guidewire may be put in place, or left in place if used to guide the separate instrument, and the separate instrument withdrawn over the guidewire.

A medical device 100, 200, 300, 400, according to the various embodiments described above, loaded on a delivery catheter, may be inserted over the guidewire, and the medical device then deployed according to the steps outlined below.

The distal portion of the medical device 100, 200, 300, 400 may then be further advanced distally beyond the lumen of the delivery catheter (which may or may not also include tissue-penetrating element), and/or an outer sheath of the delivery catheter may be retracted from the medical device, such that the distal retention member is fully deployed within the second body lumen and the surface of the distal retention member is placed in contact with the inner surface of the tissue wall of the second body lumen. The delivery catheter may then be further proximally retracted into the first body lumen, and the proximal portion of the medical device 100, 200, 300, 400 advanced distally beyond the lumen of the delivery catheter, and/or the outer sheath of the delivery catheter may be further retracted from about the medical device, such that the proximal retention member is fully deployed within the first body lumen and the surface of the proximal retention member is placed in contact with the inner surface of the tissue wall.

Alternatively, a medical device 500, 600 of the present disclosure may be disposed in the expanded configuration within the lumen of a delivery catheter including an outer sheath. A distal end of the delivery catheter may be advanced into an open interior passage of a conventional drainage device previously positioned between a first and second body lumen, using the steps outlined above. In various embodiments, the delivery catheter may be advanced to the site of the previously positioned drainage device under endoscopic guidance. The distal portion of the medical device 500, 600 may then be advanced distally beyond the lumen of the delivery catheter, and/or the outer sheath of the delivery catheter may be retracted from about the medical device, such that the distal retention member is fully deployed within a distal portion of the open interior passage of the conventional medical device, and the surface of the distal retention member is placed in contact with the inner surface of the open interior passage. The proximal portion of the medical device 500, 600 may then be advanced distally beyond the lumen of the delivery sheath, and/or the outer sheath of the delivery catheter may be further retracted from about the medical device, such that the proximal retention member is fully deployed within a proximal portion of the open interior passage of the conventional medical device and the surface of the proximal retention member is placed in contact with the inner surface of the open interior passage.

The elongate tubular body of any of the medical devices 100, 200, 300, 400, 500, 600 depicted in FIGS. 1A-9B may be formed of one or more braided filaments (e.g., nitinol wire, etc.). The proximal retention member, distal retention member, cylindrical saddle region, nose cone and/or internal cone may further include a membrane, covering or coating on an inner and/or outer surface thereof to define a contiguous open interior passage configured for controlled flow (e.g., body fluids, materials, and the like) and/or access therethrough. The coating may comprise a variety of non-degradable and biocompatible polymeric materials (e.g., upon exposure to bodily fluids such as bile), including, for example, silicones, rubbers, polyethylenes, PVDF, Chronoflex® and thermoplastic elastomers, such that the coating conforms to the medical device in the unexpanded and expanded configurations.

The proximal and distal retention members of any of the medical devices 100, 200, 300, 400, 500, 600 depicted in FIGS. 1A-9B may include various configurations, such that one or more of the retention members extend radially at an angle from the longitudinal axis of the elongate tubular body that is not necessarily perpendicular to the elongate tubular body and/or the surfaces are not necessarily planar. In various embodiments, the angle of the retention members relative to the circumference and longitudinal axis of the elongate tubular body may assume other degrees (e.g., 30, 45, 60, 75 degrees, etc.) or may change degrees along the length of the retention members creating inflection points in the retention members. For example, one or both of the proximal and distal retention members may extend outward towards an end of the elongate tubular body, back towards a center portion of the elongate tubular body, or change directions in some combination of both.

For example, one or both of the proximal and distal retention members may flare away from a longitudinal axis of the cylindrical saddle region into flange configurations on opposite ends of the cylindrical saddle region when in the expanded configuration. Each flange configuration may include at least first and second points of inflection that may define first and second segments of the flange. The first segment may extend from the first inflection point toward a center plane perpendicular to the longitudinal axis of the tubular body, and the second segment may extend from the first inflection point away from the center plane. An angle of the first inflection point defined by the first segment and the cylindrical saddle region may be at least as great as an opposing angle of the second inflection point defined by the first segment and the second segment.

As another example, each flange may include at least first and second points of inflection that define first and second segments of the flange, wherein the second points of inflection may be further spaced radially from the longitudinal axis than the first points of inflection, and the second points of inflection may be closer than the first points of inflection to a center plane along the longitudinal axis. The flanges on opposite ends of the cylindrical saddle region may touch planes that are parallel to the longitudinal axis, at least one plane each above and below the longitudinal axis, at at least two separate points along the parallel planes.

As yet a further example, each flange configuration may include at least first and second points of inflection that define first and second segments of the flange. The first segment may extend from the first inflection point toward a center plane perpendicular to the longitudinal axis of the tubular body, and the second segment may extend from the second inflection point away from the center plane. The intersection of the cylindrical saddle region and the first segments may define the first inflection points, and the intersection of the first segments and second segments may define second inflection points. An angle of the first inflection points may be 90 degrees or less, and an opposing angle of the second inflection points may be 90 degrees or less.

In various embodiments, one or both of the proximal and distal retention members may include an outer diameter $d_1$ that is greater than an outer diameter $d_2$ of the cylindrical saddle region. For example, outer diameter $d_1$ may be as much as 75%-100% greater than an outer diameter $d_2$ of the cylindrical saddle region. By way of non-limiting example, outer diameter $d_1$ may be approximately 7.0 mm to approximately 30 mm, and outer diameter $d_2$ may be approximately 3.0 mm to approximately 15.0 mm. In various embodiments, the size (e.g., diameter) of the opening formed between the first and second body lumens may be increased or decreased by increasing or decreasing the size (e.g., width) of the proximal and distal retention members (e.g., increasing or decreasing the surface area of the tissue layers compressed between the proximal and distal retention members). In addition, or alternatively, a length of the elongate tubular body in the expanded configuration may be foreshortened, e.g., at least 40% shorter than a length of the elongate tubular body when in the unexpanded configuration.

Various embodiments, e.g., the medical devices 100, 200, 300, 400, of the present disclosure, may include a double-walled flange as the proximal and distal retention members at either end of the elongate tubular body in the expanded configuration. In various other embodiments, the proximal and/or distal retention members may include a variety of other configurations, including, but not limited to single-walled flange structures at either end, and/or more than one single-walled or double-walled flange structure at either end. The walls of the flanges above and/or below the longitudinal axis may be symmetrical or may be asymmetrical. The walls of the flanges above and/or below the longitudinal axis may have multiple inflection points, as mentioned above, that define segments of the walls of the flange that change direction as the walls extend radially away from the longitudinal axis (e.g., segments can extend radially parallel to, away from and/or toward, a radial center line of the body). The segments may extend along a straight line or may be curved, or may include a combination of straight lines and curves.

In various embodiments, the direction of the nose cone or internal cone may be reversed, e.g., such that a portion of the nose cone or internal cone tapers in diameter toward the proximal retention member, to prevent or minimize the flow or fluid and/or debris from the first body lumen into the second body lumen (e.g., retrograde flow or reflux). In addition, or alternatively, in various embodiments, any of the medical devices disclosed herein may positioned within a patient such that the proximal retention member is placed in contact with the tissue wall of the second body lumen, and the distal retention member is placed in contact with the tissue wall of first body lumen to effectuate the same purpose to prevent or minimize the flow or fluid and/or debris from the first body lumen into the second body lumen (e.g., retrograde flow or reflux).

In various embodiments, any of the woven, braided and/or knitted filaments, which comprise the elongate tubular body, nose cone and/or internal cone may include a variety of different cross-sectional shapes (e.g., oval, round, flat, square, etc.) and may be formed from metals and/or polymers, including shape memory metals and polymers. The woven, braided and/or knitted filament may further include a single filament woven upon itself, or multiple filaments woven together.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device comprising:
an elongate tubular body comprising a proximal portion, a distal portion, and a length therebetween, the elongate tubular body defining a lumen along the length;
wherein:
the elongate tubular body has an unexpanded configuration, and an expanded configuration in which the proximal portion of the elongate tubular body expands into a proximal retention member and the distal portion of the elongate tubular body expands into a distal retention member leaving a cylindrical saddle region extending therebetween; and
the elongate tubular body includes a constricted portion formed by a plurality of filament loops, each loop having a radially-inwardly directed distal free end, the distal free ends of the filament loops overlapping one another to form a tapered cone shape with the loops movable with respect to one another between a first diameter configuration in which the loops overlap one another to inhibit flow through the saddle region, and a second diameter configuration larger than the first diameter configuration to provide an open flow or access passage therethrough.

2. The medical device of claim 1, wherein the radially-inwardly directed overlapping filament loops are configured to move from the first diameter configuration to the second diameter configuration in response to a threshold level of force applied thereto.

3. The medical device of claim 1, wherein the constricted portion is positioned at a midpoint of the cylindrical saddle region.

4. The medical device of claim 1, wherein the distal retention member, proximal retention member and cylindrical saddle region are covered.

5. The medical device of claim 1, wherein the elongate tubular body is formed of one or more braided filaments.

6. The medical device of claim 1, wherein an outer surface of the proximal retention member, an outer surface of the distal retention member, or both, is configured to interface with an inner surface of a drainage stent.

7. A medical device, comprising:
an elongate tubular body comprising a proximal portion, a distal portion, and a length therebetween, the elongate tubular body defining a lumen along the length, the elongate tubular body having an unexpanded configuration, and an expanded configuration wherein the proximal portion expands into a proximal retention member and the distal portion expands into a distal retention member leaving a cylindrical saddle region therebetween; and
a plug comprising radially-inwardly directed overlapping filament loops circumferentially positioned with respect to one another in a tapered shape having distal free ends configured to move between an overlapped closed configuration in which the distal ends of the filament loops are overlapped and contact one another in a tapered configuration inhibiting flow through the cylindrical saddle region, and an open configuration allowing access through the cylindrical saddle region.

8. The medical device of claim 7, wherein an outer diameter of the plug is equal to or greater than an inner diameter of the cylindrical saddle region.

9. The medical device of claim 7, wherein an outer surface of the proximal retention member, an outer surface of the distal retention member, or both, is configured to interface with an inner surface of a drainage stent.

10. A medical device, comprising:
an elongate tubular body formed of braided filaments and comprising a proximal portion, a distal portion, and a length extending therebetween, the elongate tubular body forming a lumen along the length, the elongate tubular body having an unexpanded configuration, and an expanded configuration wherein the proximal portion expands into a proximal retention member, the distal portion expands into a distal retention member, and a cylindrical saddle region extends therebetween; and
a cone attached to or integrally formed with a portion of the elongate tubular body, wherein the cone is formed of radially-inwardly directed filament loops structurally distinct from the braided filaments of the elongate tubular body, the filament loops having radially-inwardly directed distal free ends configured to move between an overlapped conical configuration with the distal ends of the filament loops contacting one another and having a first diameter configuration limiting flow through the lumen of the elongate tubular body, and an enlarged second diameter configuration allowing access through the lumen of the elongate tubular body.

11. The medical device of claim 10, wherein the cone is configured to move from the first diameter configuration to the enlarged second diameter configuration in response to a threshold level of force applied to the cone.

12. The medical device of claim 10, wherein the proximal retention member, distal retention member, cylindrical saddle region and cone are covered.

13. The medical device of claim 10, wherein the elongate tubular body is formed of one or more braided filaments, and wherein the cone is integrally formed with the one or more braided filaments.

14. The medical device of claim 13, wherein the radially-inwardly directed overlapping filament loops of the cone are integrally formed with the one or more braided filaments.

15. The medical device of claim 13, wherein the cone is an internal cone disposed within the cylindrical saddle region.

16. The medical device of claim 15, wherein the internal cone is positioned at a midpoint of the cylindrical saddle region.

17. The medical device of claim 15, wherein the internal cone includes a portion that tapers in diameter toward the distal retention member.

18. The medical device of claim 10, wherein the cone is a nose cone attached to and extending distally beyond the distal retention member.

* * * * *